United States Patent

Landscheidt et al.

[11] Patent Number: 5,478,960
[45] Date of Patent: Dec. 26, 1995

[54] PROCESS FOR THE PREPARATION OF HETEROSUBSTITUTED ACETALS

[75] Inventors: Heinz Landscheidt, Duisburg; Alexander Klausener, Cologne, both of Germany

[73] Assignee: Bayer Aktiengesellschaft, Leverkusen, Germany

[21] Appl. No.: 408,240

[22] Filed: Mar. 22, 1995

[30] Foreign Application Priority Data

Mar. 29, 1994 [DE] Germany ............... 44 10 867.2

[51] Int. Cl.⁶ ............................ C07F 9/02
[52] U.S. Cl. .................. 558/51; 558/87; 558/89; 558/104; 558/113; 558/114; 558/117; 558/118; 558/186; 568/32
[58] Field of Search .................. 558/51, 87, 89, 558/104, 113, 114, 117, 118, 186; 568/32

[56] References Cited

U.S. PATENT DOCUMENTS 4,947,005  8/1990  Koeffer et al. ................ 558/51

FOREIGN PATENT DOCUMENTS

| 0055108 | 6/1982 | European Pat. Off. . |
| 55108 | 6/1982 | European Pat. Off. . |
| 359118 | 3/1990 | European Pat. Off. . |

OTHER PUBLICATIONS

CA 118:147196g Preparation . . . carbonates. Landscheidt et al., p. 802, 1993.
T. Izumi, et al. J. Heterocyclic Chem. vol. 29, 1625–1629 (1992).
A. Kamimura, Synthesis, vol. 90(8), p. 694; 1984.
T. Bychkova et al., Zh. Org. Khim., vol. 20, No. IV, pp. 2114–2118 (1985).
M. Halmann, et al., J.C.S. Perkin II, pp. 1210–1213, (1976).
E. Gehrer, Synthesis, vol. 87(7), pp. 633–635 (1987).
N. Simpkins, Tetrahedron Letters, vol. 28, No. 9, pp. 989–992 (1987).
F. Barbut et al., Bull. Soc. Chem. Fr. vol. 83, Part II, pp. 41–45 (1982).

*Primary Examiner*—Joseph K. McKane
*Attorney, Agent, or Firm*—Sprung Horn Kramer & Woods

[57] ABSTRACT

Heterosubstituted acetals of the formula $$\begin{array}{c} R^1O \\ \phantom{R^1O}\diagdown \\ \phantom{R^1OO}CH-CH_2-A^1, \\ \phantom{R^1O}\diagup \\ R^1O \end{array} \quad (I)$$

can be obtained by reacting vinyl compounds of the formula $$CH_2=CH-A^1 \quad (II)$$

with alkyl nitrites of the formula $$R^1-ONO \quad (III)$$

The reaction is performed in the presence of palladium in metallic or bonded form and in alcohols or ethers as reaction medium at from 0° to 120° C.

10 Claims, No Drawings

PROCESS FOR THE PREPARATION OF HETEROSUBSTITUTED ACETALS

BACKGROUND OF THE INVENTION

1. Field of the Invention

The present invention relates to a process for the preparation of heterosubstituted acetals by reaction of heterosubstituted vinyl compounds with alkyl nitrites in the presence of palladium in metallic or bonded form.

Heterosubstituted acetals of the formula (I) specified later on below are suitable as starting materials for the synthesis of other organic compounds, such as medicaments, plant protection agents or dyes. Thus, for example, diethyl 2,2-dimethoxyethylphosphonate can be employed for the chain lengthening of ketones and aldehydes (Org. Synth. 53 (1973), 44–48). The transacetalization of this compound leads, furthermore, to phosphorus-containing polymers (J. Polym. Sci. 22 (1984), 3335–3342; J. Polym. Sci. A 26 (1988), 2997–3014); polymers of this type are employed in the sectors of flameproofing agents, hydrometallurgy and membrane technology.

Phenylsulphonyl-acetaldehyde diethyl acetal is reacted in accordance with DE-A 34 19 750 to give precursors for the preparation of pyrethroids.

Phenoxysulphonyl-acetaldehyde dialkyl acetal can be converted to 1,2-benzoxathiine 2,2-dioxide, which can be reacted in accordance with EP 128 116 and EP 337 947 to give herbicides.

2. Description of the Related Art

The literature describes with sporadic cases the preparation of acetals by reaction of the parent olefins with alkyl nitrites in the presence of palladium salts. Thus, for example, EP 55 108 describes the oxidation of compounds such as ethene, propene, butylene, cyclohexene, acrylic esters and acrylonitrile. The yields obtained in these oxidations, however, are low, so that any industrial utilisation would have to take account of considerable expenditure on production isolation and on the recycling of catalyst and solvent. In particular, the gas phase reaction proposed in EP 55 108 cannot be used for preparing acetals of the formula (I) specified later on below, since at the high temperature necessary for this reaction the occurrence of decomposition reactions and other secondary reactions would have to be expected.

J. Heterocyclic Chem. 29(1992), 1625 describes the reaction of 2-nitro-styrenes with alkyl nitrites in liquid phase, with the simultaneous addition of oxygen, to give the corresponding acetals. However, this reaction may give rise to ignitable mixtures, a fact which—especially in the case of industrial implementation—leads to a relatively high expenditure for the provision of the necessary safety measures.

The literature consequently contains only processes which can be used to react unsubstituted olefins, or olefins which are mono- or disubstituted on at least one carbon atom with a further carbon atom; in particular, the literature contains no processes which can be used to convert heterosubstituted vinyl compounds to acetals. Owing, however, to the many possible applications of heterosubstituted acetals, there was a need to provide processes for their preparation.

SUMMARY OF THE INVENTION

It has now been found that vinyl compounds of the formula (II) specified later on below can, surprisingly, be reacted in high yields, by reaction with alkyl nitrites under the conditions of the process according to the invention, to give acetals of the formula (I).

The invention relates to a process for the preparation of heterosubstituted acetals of the formula

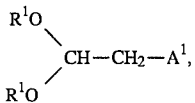  (I)

in which

R$^1$ represents straight-chain or branched C$_1$–C$_8$-alkyl, preferably C$_1$–C$_2$-alkyl, particularly preferably methyl, and A$^1$ represents a heteroatom from the group consisting of silicon, oxygen, sulphur, selenium, tellurium, nitrogen and phosphorus, which, within the scope of its bonding ability, carries one or more identical or different substituents from the group consisting of double-bonded oxygen, C$_1$–C$_8$-alkoxy, C$_1$–C$_8$-alkyl, aryloxy, substituted aryloxy, aryl and substituted aryl, and may in addition carry a positive charge, which is characterized in that vinyl compounds of the formula

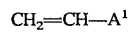  (II), in which

A has the above meaning, are reacted, in the presence of palladium in metallic or bonded form and in alcohols or ethers or mixtures of two or more of them as reaction medium at from 0 to 120° C., preferably from 40° to 80° C., with alkyl nitrites of the formula

R$^1$—ONO  (III), in which

R$^1$ has the above meaning.

DETAILED DESCRIPTION OF THE INVENTION

Straight-chain or branched C$_1$–C$_8$-alkyl is, for example, methyl, ethyl, propyl, isopropyl, butyl, isobutyl, tert-butyl, the isomeric pentyls, hexyls, heptyls and octyls. Alkyl is preferably methyl or ethyl, particularly preferably methyl.

Straight-chain or branched C$_1$–C$_8$-alkoxy is, for example, methoxy, ethoxy, propoxy, isopropoxy, butoxy, isobutoxy, tert-butoxy, the isomeric pentyloxy, hexyloxy, heptyloxy and octyloxy. C$_1$–C$_4$-alkoxy is preferred, and methoxy and ethoxy are particularly preferred.

Aryl has 6 to 12 carbon atoms and is, for example, phenyl, biphenylyl or naphthyl. Aryl can be substituted by from 1 to 3 identical or different substituents consisting of methyl, ethyl, methoxy, ethoxy, chlorine and bromine. Aryloxy likewise has 6 to 12 carbon atoms and is derived from the aryl described, in unsubstituted or substituted form.

A$^1$ is a heteroatom from the group consisting of silicon, oxygen, sulphur, selenium, tellurium, nitrogen and phosphorus, preferably from the group consisting of silicon, oxygen, sulphur, nitrogen and phosphorus and with particular preference from the group consisting of sulphur and phosphorus.

Accordingly, preferred vinyl compounds are those of the formula

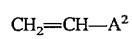  (IV)

where $A^2$ denotes a substituted heteroatom from the group consisting of silicon, oxygen, sulphur, nitrogen and phosphorus.

Particularly significant vinyl compounds are those from the group consisting of $$CH_2=CH-\underset{R^4}{\overset{R^2}{\underset{|}{\overset{|}{Si}}}}-R^3$$

$$CH_2=CH-O-R^2$$

$$CH_2=CH-\overset{R^2}{\underset{|}{N}}-R^3$$

$$CH_2=CH-\underset{R^4\ \ X^-}{\overset{R^2}{\underset{|}{\overset{|}{N^+}}}}-R^3$$

$$CH_2=CH-\overset{R^2}{\underset{|}{P}}-R^3$$

$$CH_2=CH-\underset{R^4\ \ X^-}{\overset{R^2}{\underset{|}{\overset{|}{P^+}}}}-R^3$$

$$CH_2=CH-\underset{\overset{\|}{O}}{\overset{R^2}{\underset{|}{P}}}-R^3$$

$$CH_2=CH-S-R^2$$

$$CH_2=CH-\overset{O}{\underset{\|}{S}}-R^3$$

$$CH_2=CH-\underset{\overset{\|}{O}}{\overset{O}{\underset{\|}{S}}}-R^2$$

In these particularly significant vinyl compounds, $R^2$, $R^3$ and $R^4$ denote independently of one another straight-chain or branched $C_1$–$C_8$-alkoxy, $C_1$–$C_8$-alkyl, $C_6$–$C_{12}$-aryloxy or $C_6$–$C_{12}$-aryl, in which case aryl and/or aryloxy may be substituted in the above manner. Where the heteroatom carries a positive charge, as is evident from the above formulations, such a compound contains an anion $X^-$ which denotes chloride, bromide, ½ sulphate, nitrate, acetate, trifluoroacetate, formate, propionate or benzoate. From the series of the above, particularly significant vinyl compounds listed by way of their formulae, the following are preferred:

$$CH_2=CH-\underset{\overset{\|}{O}}{\overset{O}{\underset{\|}{S}}}-O-R^5$$

$$CH_2=CH-\underset{\overset{\|}{O}}{\overset{\overset{R^5}{\underset{|}{O}}}{\underset{|}{P}}}-O-R^6$$

-continued $$CH_2=CH-\underset{\overset{\|}{O}}{\overset{O}{\underset{\|}{S}}}-R^5$$

In these formulae $R^5$ and $R^6$ independently of one another denote methyl, ethyl or phenyl.

Palladium may be employed in metallic or bonded form. When palladium is used in metallic form it may be transformed, at least in part, into the bonded form during the reaction according to the invention. Preferably, however, palladium in bonded form is employed. The bonded form comprises both simple salts and complex salts and also complex compounds in which the palladium has the valency zero. Such palladium salts should be wholly or partially soluble in the reaction mixture. Examples of palladium salts which may be mentioned are palladium chloride, palladium bromide, palladium acetate, palladium trifluoroacetate, palladium salts of organic carboxylic acids such as propionic acid, benzoic acid or other aliphatic or other aromatic carboxylic acids, palladium salts of heteropoly acids, especially palladium salts of the heteropoly acids derived from vanadium, molybdenum, niobium and tungsten. Preferably suitable palladium compounds are the palladium halides mentioned, and in particular palladium chloride. Palladium in bonded form, especially palladium in the form of the salts mentioned, can be supplemented by salts of other metals, such as the alkali metals or alkaline earth metals or salts of ammonium or of amines with different degrees of substitution. Suitable anions for such salts include those specified above for the palladium. Many of these salts form complexes with palladium in bonded form, so that they are also examples of the abovementioned complex salts of palladium. Supplementary salts of this kind are preferably lithium chloride or sodium chloride, preferably lithium chloride.

Alcohols and ethers which are suitable for the implementation of the process according to the invention are $C_1$–$C_4$-alkanols, such as methanol, ethanol, propanol, iso-propanol, butanol, isobutanol or tert-butanol, and also ethylene glycol, 1,2- or 1,3-propylene glycol or 1,2-, 1,3-, 1,4- or 2,3-butylene glycol, their ethers or semiethers with one another, such as ethylene glycol dimethyl ether or diethylene glycol, and also dioxane or tetrahydrofuran. Ethers of these substances with one another furthermore comprise compounds such as diisopropyl ether, dibutyl ether, and diethylene glycol mono- and diethyl ether. In order to simplify the reaction regime and the working-up procedure, it is preferred to work in one of the $C_1$–$C_4$-alkanols mentioned. It is particularly preferred to work in the alkanol on which the alkyl nitrite used for the reaction according to the invention is based.

Examples of the alkyl nitrite which may be mentioned are methyl nitrite, ethyl nitrite, propyl nitrite, isopropyl nitrite, butyl nitrite or isobutyl nitrite.

The process according to the invention is carried out at a temperature in the range of 0° to 120° C., preferably from 40° to 80° C. The pressure at which the reaction according to the invention is carried out is not critical and may be in the range of 0.5–10 bar, preferably 1.0–6 bar and particularly preferably 1–5 bar. However, it is also possible to work at higher or lower pressures.

For the implementation of the reaction it is possible, for example, first of all to suspend or wholly or partially dissolve the palladium, in metallic or bonded form, in one of the solvents mentioned. The vinyl compound, mixed if desired with a portion of the relevant solvent, is added to this suspension or total or partial solution at the stated temperature. The alkyl nitrite is then added, continuously or in portions, in liquid or in gaseous form. It is also possible, however, to add the vinyl compound and the alkyl nitrite simultaneously. When, as preferred, methyl nitrite is employed, it is expediently passed into the reaction solution as a mixture with an inert gas. Suitable examples of the inert gas are nitrogen, argon or carbon dioxide, preferably nitrogen. In the case where other alkyl nitrites are used it may also be sensible, for example on considerations of safety, to work in the presence of an inert gas. The quantity of solvent is from 1 to 100 mol, preferably from 5 to 40 mol, per mol of vinyl compound employed.

The molar ratio of the vinyl compound (II) to the alkyl nitrite (III) is from 1:1 to 1:10, preferably from 1:1.5 to 1:5.

The quantity of the palladium in metallic or bonded form, calculated as metal, is from 0.001 to 0.2 g-atom, preferably from 0.001 to 0.1 g-atom, per mol of vinyl compound.

The reaction products are isolated and worked up in a manner familiar to the person skilled in the art, for example by distillation of the solvent followed by precision distillation of the reaction product under reduced pressure, by crystallization or by a combination of these measures, as well as by chromatography if desired.

EXAMPLES

Example 1

A mixture of 200 ml of methanol, 0.4 g (2.3 mmol) of palladium chloride and 0.2 g (4.7 mmol) of lithium chloride was heated to 60° C.

Subsequently the continuous introduction of a stream of gas comprising 10 l/h of nitrogen and 0.2 mol/h of methyl nitrite was commenced.

After 15 min, 32.8 g (0.2 mol) of diethyl vinylphosphonate were added dropwise over the course of 10 minutes.

For a further 2 hours methyl nitrite was passed in in a stream of nitrogen, so that a total of about 0.5 mol of methyl nitrite was consumed.

When the introduction of methyl nitrite had ended, the mixture was stirred for 1 hour in a stream of nitrogen.

Methanol was distilled off from the solution and the residue was distilled in vacuo.

38.2 g of diethyl 2,2-dimethoxy-ethylphosphonate were obtained (85% of theory). Boiling point: 90°–92° C./1 mbar.

Example 2

A mixture of 200 ml of methanol, 0.25 g (1.4 mmol) of palladium chloride and 0.125 g (2.9 mmol) of lithium chloride was heated to 60° C.

Subsequently the continuous introduction of a stream of gas comprising 10 l/h of nitrogen and 0.1 mol/h of methyl nitrite was commenced.

After 15 min, 8.4 g (0.046 mol) of phenyl vinylsulphonate, dissolved in 20 ml of methanol, were added dropwise.

For a further 2 hours methyl nitrite was passed in, so that a total of about 0.2 mol of methyl nitrite was consumed.

When the introduction of methyl nitrite had ended, the mixture was stirred for 1 hour in a stream of nitrogen.

Methanol was distilled off from the solution and the residue was distilled in vacuo.

9.1 g of phenyl 2,2-dimethoxyethyl sulphonate were obtained (81% of theory). Boiling point: 135° C./0.5 mbar.

Example 3

400 mg (2.3 mmol) of palladium chloride and 200 mg (4.7 mmol) of lithium chloride were dissolved with heating at 60° C. in 240 ml of methanol.

Subsequently a continuous gas stream comprising 10 l/h of nitrogen and 0.2 mol/h of methyl nitrite was introduced.

After 15 min, a solution of 30 g (0.18 mol) of phenyl vinyl sulphone in 60 ml of methanol was added dropwise.

For a period of 2 hours more methyl nitrite was passed in, so that a total of about 0.4 mol of methyl nitrite was consumed.

Methanol was distilled off from the solution and the residue was distilled in vacuo.

31.6 g (0.14 mol) of 2,2-dimethoxy-ethyl phenyl sulphone were obtained (77% of theory). Boiling point: 139–140° C./0.7 mbar.

What is claimed is:

1. A process for the preparation of a heterosubstituted acetal of the formula

in which

R¹ represents straight-chain or branched $C_1$–$C_8$-alkyl, and

A¹ represents a heteroatom from the group consisting of silicon, oxygen, sulphur, selenium, tellurium, nitrogen and phosphorus, which, carries one or more identical or different substituents selected from the group consisting of double-bonded oxygen, $C_1$–$C_8$-alkoxy, $C_1$–$C_8$-alkyl, aryloxy, substituted aryloxy, aryl and substituted aryl, and may in addition carry a positive charge, wherein a vinyl compound of the formula

in which

A¹ has the above meaning, is reacted, in the presence of palladium in metallic or bonded form and in an alcohol or an ether or a mixture of two or more of them as reaction medium at from 0° to 120° C. with an alkyl nitrite of the formula

in which

R¹ has the above meaning.

2. The process of claim 1, wherein a vinyl compound of the formula

is employed, in which

A² represents a substituted heteroatom from the group consisting of silicon, oxygen, sulphur, nitrogen and phosphorus, which may in addition carry a positive charge.

3. The process of claim 2, wherein a vinyl compound from the group consisting

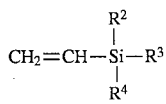

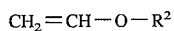

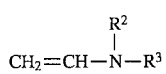

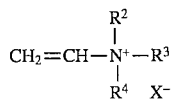

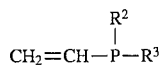

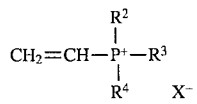

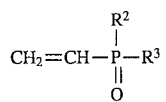

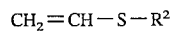

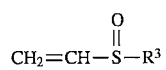

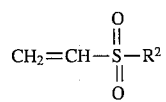

is employed, in which
 $R^2$, $R^3$ and $R^4$ represent independently of one another straight-chain or branched $C_1$–$C_8$-alkoxy, $C_1$–$C_8$-alkyl, $C_6$–$C_{12}$-aryloxy, substituted $C_6$–$C_2$-aryloxy, $C_6$–$C_{12}$-aryl or substituted $C_6$–$C_{12}$-aryl, and
 $X^-$ denotes chloride, bromide, ½ sulphate, nitrate, acetate, trifluoroacetate, formate, propionate or benzoate.

4. The process of claim 3, wherein a vinyl compound from the group consisting of

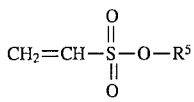

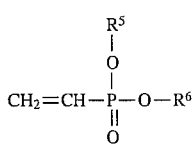

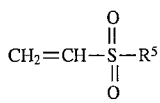

is employed, in which
 $R^5$ and $R^6$ denote independently of one another methyl, ethyl or phenyl.

5. The process of claim 1, wherein palladium is employed in bonded form, which may be converted into a complexed form by addition of a further salt.

6. The process of claim 5, wherein palladium in bonded form is a palladium halide.

7. The process of claim 6, wherein the palladium halide is palladium chloride.

8. The process of claim 1, wherein $R^1$ represents $C_1$–$C_2$-alkyl.

9. The process of claim 8, wherein $R^1$ represents methyl.

10. The process of claim 1, wherein the reaction is carried out at from 40° to 80° C.

* * * * *

UNITED STATES PATENT AND TRADEMARK OFFICE
CERTIFICATE OF CORRECTION

PATENT NO. : 5,478,960

DATED : December 26, 1995

INVENTOR(S) : Landscheidt, et al.

It is certified that error appears in the above-identified patent and that said Letters Patent is hereby corrected as shown below:

Col. 7, line 2      After " consisting " insert -- of --

Col. 7, last line    Delete " $C_6$-$C_2$-aryloxy " and substitute -- $C_6$-$C_{12}$-aryloxy --

Signed and Sealed this

Fourth Day of June, 1996

Attest:

BRUCE LEHMAN

Attesting Officer      Commissioner of Patents and Trademarks